United States Patent [19]

Ahuja

[11] Patent Number: 5,398,176
[45] Date of Patent: Mar. 14, 1995

[54] MULTIFUNCTIONAL LAMP AND SUPPORT

[76] Inventor: Sushil K. Ahuja, 163 Johnson Ct., Whitehall, Pa. 18052

[21] Appl. No.: 49,112

[22] Filed: Apr. 19, 1993

[51] Int. Cl.$^6$ .............................................. F21V 33/00
[52] U.S. Cl. ................................... 362/253; 362/287; 362/421; 248/160; 248/276
[58] Field of Search ............ 606/1, 2; 607/90; 248/160, 276; 362/138, 139, 253, 285, 287, 418, 419, 421

[56] References Cited

U.S. PATENT DOCUMENTS

| | | | |
|---|---|---|---|
| 354,976 | 12/1886 | Field | 248/276 |
| 504,866 | 9/1893 | Davenport | 248/160 |
| 599,543 | 2/1898 | Whitaker | 248/276 |
| 644,860 | 3/1900 | Hubert | 362/253 |
| 1,186,428 | 6/1916 | Newman | 362/421 |
| 1,279,803 | 9/1918 | Watson | 362/421 |
| 1,735,949 | 11/1929 | Brady | 248/160 |
| 2,104,198 | 1/1938 | Jones | 362/421 |
| 2,204,508 | 6/1940 | Matthies | 248/160 |
| 2,510,198 | 6/1950 | Tesmer | 248/160 |
| 2,533,494 | 12/1950 | Mitchell, Jr. | 248/276 |
| 4,023,757 | 5/1977 | Allard et al. | 248/160 |
| 4,630,185 | 12/1986 | Copeland | 362/427 |
| 4,853,965 | 8/1989 | Blonski | 248/160 |
| 4,870,964 | 10/1989 | Bailey, Jr. et al. | 606/1 |
| 4,885,667 | 12/1989 | Selden | 362/253 |
| 4,907,137 | 3/1990 | Schladitz et al. | 362/145 |

*Primary Examiner*—Stephen F. Husar
*Assistant Examiner*—Alan B. Cariaso

[57] ABSTRACT

This invention relates to an improved multifunctional lamp particularly suited for use in medical facilities as, for example, by pathologists in the evaluation of tissues and fluids, etc. The basic lamp systems contemplated herein comprises a base, a trunk supported at an end by the base and illumination means pendent from the trunk. The improvement of this basic lamp, and the adaption of it for medical purposes comprises the following:

a lamp having a flexible trunk section for rotation and movement about its base and relative to its longitudinal axis, thereby permitting the user to move the lamp and associated apparatus into position for use;

a lamp having a safety shield which is pendent from a flexible arm for movement about the axis of the arm and the trunk thereby permitting the user to strategically place the safety shield in a fixed position for providing protection; and, a lamp equipped with means for review of microscopic organisms, etc which is pendent form a flexible arm for movement about the trunk.

The tubular trunk is supported at one end by the base formed from a plurality of interconnecting tubular connectors joined end to end, each tubular connector having a ball portion at one end and a socket portion at the other end, said ball portion adapted for embracement by a socket portion associated with an adjoining connector. A plurality of Tee-connectors having distal ball or socket portions or both adapted for receipt by a corresponding socket or ball portion from tubular connectors are associated with the trunk portion of said lamp, said Tee-members adapted for rotation and movement about the longitudinal axis of the trunk. Communicating with a Tee connector is a first tubular arm comprising a plurality of connectors having ball and socket portions for engagement with the ball or socket member of said arm a Tee-member or connector and terminating in means for engaging a safety shield and a second tubular arm comprising a plurality of ball and socket members engaging a Tee-connectors and terminating in means for magnification.

10 Claims, 1 Drawing Sheet

U.S. Patent  Mar. 14, 1995  5,398,176
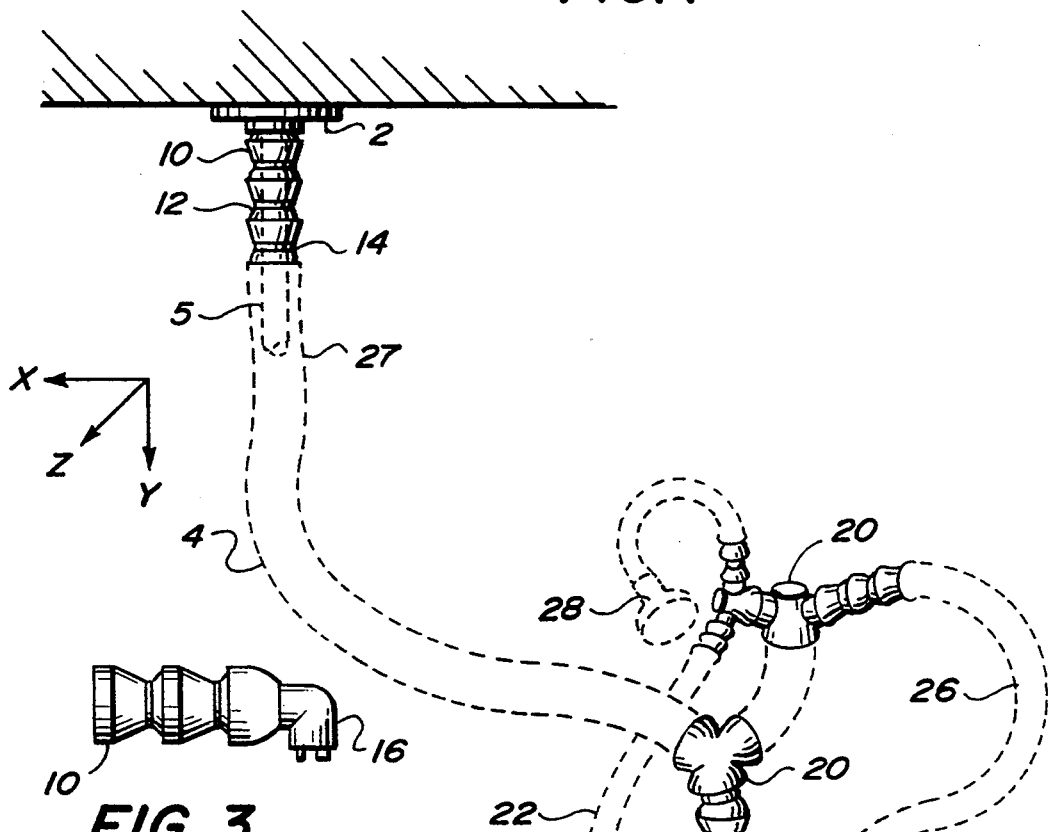
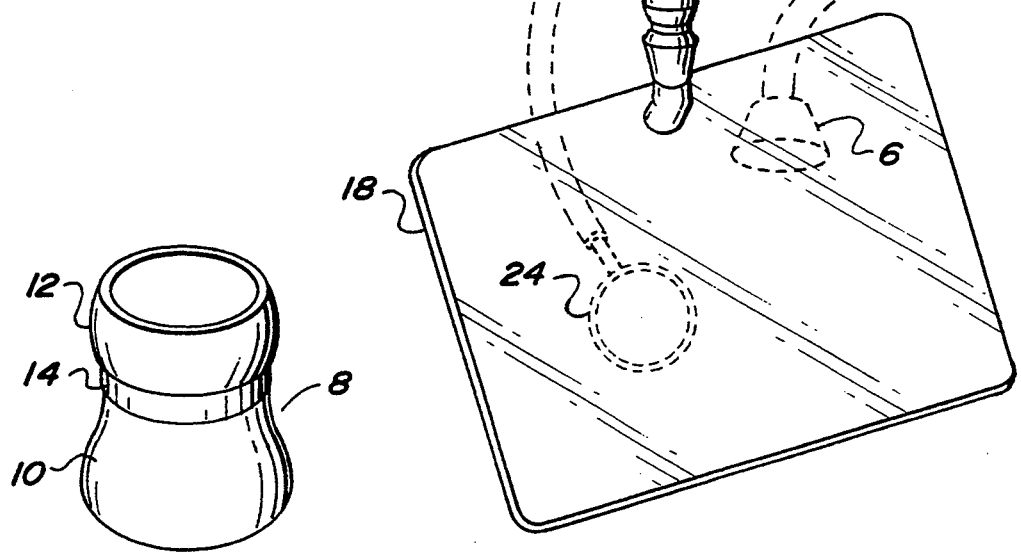

MULTIFUNCTIONAL LAMP AND SUPPORT

FIELD OF THE INVENTION

This invention relates to lamps particularly suited for the medical profession and to the supporting system.

DESCRIPTION OF THE PRIOR ART

Lighting fixtures, as is known, come in all sorts of sizes, shapes and may include other elements designed to perform a variety of functions. In many fields of endeavor it is required that the lamps be supported by flexible and rotatable means associated therewith so that the position of the lamp can be moved and "locked" into position at the discretion of the user. Other functions may also be desirable in lamps depending on the field of use.

The medical field has numerous requirements for lighting equipment, including ease of use and access to instrumentation. Pathologists, for example, are required to effect close visual and magnified evaluation of body tissue and fluids which may contain highly contagious viruses, bacteria, fluid borne pathogens and the like. It is important that exposure to these possibly infectious tissues and fluids be minimized. With enhanced concern regarding exposure to the HIV virus, proposed amendments for occupational health and safety, such as in pathology and surgery require this work to be carried out behind a protective face shield or covering so that the user is not exposed to contamination by spillage, splashing, or splattering of the fluids. Much of this work in the medical field also requires a detailed analysis of the tissue or fluid often leading to extensive note taking based upon observations made during the investigation. Often means for transcribing notes and observations at the time of the analysis are utilized.

Representative lamp configurations having flexible and rotatable means are represented in the following patents:

U.S. Pat. No. 4,907,137 discloses an apparatus for supporting a lamp on a low-voltage rail. The lamp shown is one capable of being displaced and clamped at arbitrary locations along a rail. The lamp includes a clamping socket, illumination means, and an extension part or neck consisting of a plurality of serially connected joint members, each having a ball portion and a joint seat portion, with the individual ball portion of each joint member held in the joint seat portion of associated joint members via friction. In a preferred mode, a pin is disposed transverse to the longitudinal axis so that the joint members rotate as a single unit.

U.S. Pat. No. 4,630,185 discloses a support member for illumination means comprising a mechanical arm which permits the lamp to be maintained in a free position. A pair of tubular members are rotatably attached to a base and carried in parallel relationship to each other with a means for illumination attached at the distal end of the parallel members. In a preferred embodiment the illumination means comprises two attachment points which are rotatable relative to each attachment means engaging separate arm of the lamp.

There is a need for lamps having some of the features described in the above patented systems but also including other functional elements which assist in protecting the worker and assist in evaluation of contagious material.

SUMMARY OF THE INVENTION

This invention relates to an improved multifunctional lamp particularly suited for use in medical facilities as, for example, by pathologists in the evaluation of tissues and fluids, etc and to a supporting system for such lamps. The basic lamp systems contemplated herein comprises a base, a trunk supported at an end by the base and illumination means pendent from the trunk. The improvement of this basic lamp, and the adaption of it for medical purposes, comprises the following:

- a tubular trunk supported by the base, said trunk formed from a plurality of interconnecting tubular connectors joined end to end, each tubular connector having a ball portion at one end and a socket portion at the other end, said ball portion adapted for frictional embracement by a socket portion associated with an adjoining tubular connector;
- a plurality of tubular Tee-connectors having distal ball or socket portions or both adapted for receipt by a corresponding socket or ball portion from tubular connectors associated with the trunk portion of said lamp, said tubular Tee-members adapted for rotation and flexible movement about the longitudinal axis of the trunk;
- a first tubular arm pendent from said trunk comprising a plurality of tubular connectors having ball and socket portions with an end portion adapted for engagement with the ball or socket member of said arm engaging a corresponding socket or ball portion associated with said Tee-members and terminating in means for engaging a safety shield; and,
- a second tubular arm comprising a plurality of tubular connectors having ball and socket portions with an end portion adapted for engaging socket or ball portions associated with said tubular Tee-members and an end portion terminating in means for magnification.

There are significant advantages associated with the multifunctional lamp of this invention and these advantages include:

- a lamp having a flexible trunk section for rotation and movement about its base and relative to its longitudinal axis, thereby permitting the user to move the lamp and associated apparatus into position for use;
- a lamp having a support means which permits one to essentially lock the lamp into a fixed position;
- a lamp particularly suited for pathology work, the lamp being equipped with a protective safety shield which is pendent from a flexible arm for movement about the axis of the arm and the trunk thereby permitting the user to strategically place the protective safety shield in a fixed position for providing protection;
- a lamp equipped with magnification means for review of minute organisms, etc which is pendent from a flexible arm for rotation and flexible movement about the trunk; and lastly,
- a lamp capable of carrying a microphone for utilization in transcribing observations.

THE DRAWINGS

FIG. 1 is a view of the lamp including a safety shield, magnification means and recording means having planar designations X, Y and Z associated therewith.

FIG. 2 is an isometric view of the tubular connector having ball and socket portions.

FIG. 3 is a view of a small section of an arm or trunk having an end portion having securing means.

DETAILED DESCRIPTION OF THE INVENTION

Referring to FIG. 1, the multifunctional lamp, which is particularly suited for medical offices, comprises a base 2, a trunk section 4, a rod 5 supported at an end by base 2 and illumination means 6 supported by trunk 4. In the embodiment shown, base 2 comprises a circular magnet for attachment and support of the lamp to paramagnetic surfaces such as steel. In a preferred embodiment, a small circular polymeric substrate is adhesively applied to the base of the magnet to prevent scratching of surfaces during fastening and removing the lamp from surfaces. Alternatively, base 2 could be in the form of a clamp having means for grasping a surface or other support means.

The trunk 4 comprises a plurality of tubular connectors 8 joined end to end. To facilitate an understanding of the tubular connectors utilized in forming the trunk and associated arm portions, reference is also made to FIG. 2. Each tubular connector 8 terminates in a generally circular socket portion 10 at one end and a generally circular ball portion 12 at the other. Socket portion 10 has a curved surface adapted for receipt of a ball portion 12 from an adjacent tubular connector. The tolerances between the interior surface of socket portion 10 of one connector and the exterior surface of ball portion 12 of an adjacent tubular connector are such that the ball portion is locked in place within the socket portion by means of a friction fit. Such tubular connections are shown in FIG. 1. Associated with each tubular connector 8 is a collar section 14 which has a circumference less than the circumference of the socket portion 10 and ball portion 12 of the tubular connector thereby providing space for flexible movement of the tubular connectors relative to one another.

Because of the generally circular shape of the ball and socket portion of each connector, separated by collar 14, each tubular connector, relative to an adjacent tubular connector, is capable of being rotated 360 degrees about the Y-axis. On the other hand the tubular connectors, relative to an adjacent tubular connector is rigidly held in a direction axial to the Y-axis. Also as can be seen, the connectors are positioned for movement in any direction about the X-axis or Z-axis. And, due to the friction fit between the ball portion of a tubular connector and the socket portion of an adjoining tubular connector, the trunk and arms can be moved in relation to the axis described and essentially locked into that position by means of the friction fit between adjacent tubular connectors.

An elbow 16 (FIG. 3) is attached to an end of the trunk 4 and is equipped with means for securing objects thereto, e.g., an end having a threaded portion extending therein for receipt of a screw or bolt. A protective safety shield or face shield 18 comprising glass, acrylic or a polycarbonate sheet is securely attached to the securing means by means of a screw and thus securely attached to trunk 4. The glass, polyacrylate or polycarbonate safety shield is shown attached at the center (FIG. 1) although the attachment location is largely at the discretion of the user often to provide better distribution of weight, the safety shield 18 is attached at an upper, center portion.

A plurality of Tee-members or connectors 20 (FIG. 1) terminate in ball and socket portions and are adapted for receipt by socket portion 10 or embracement by ball portion 12 thereby providing means for attaching arms 22 and 24 pendent from trunk 4. These arms generally are of smaller diameter than the diameter of trunk 4 in order to reduce the overall weight of the lamp. A plurality of connectors having alternate ball and socket sections, as was the case with trunk 4, are attached to the open end of Tee-members 20 thereby providing arms of indefinite length. Terminating at an end of arm 22 is attachment means for receipt of magnifying glass 24. By virtue of the ability to move the arm in rotation about the Y-axis and relative to the X and Z-axis, magnifying glass 24 can be moved to any position by the user for enhancing visual analysis. The ability to position magnifying glass 24 in front of or behind safety shield 18 is an advantage as it permits the user to position the magnifying glass 24 for proper focus.

As shown in FIG. 1, a second Tee-member is disposed between base 4 and elbow 16 for the purpose of establishing a pendent arm relative to trunk 4. In the embodiment shown, the arm 26 terminates in fastening means adapted for receipt of a microphone 28 which permits the user to record observations during the evaluation process. The fastening means for receipt of the microphone can include a magnet, finger clamps, a hook and the like.

The support system comprising the trunk and arms generally is made from a polymeric material by injection molding processes. The key is not so much as to how they are made but whether the connectors frictionally lock into place when moved from one point to another. Material used for the manufacture of the connectors forming the trunk and arms include polyethylene, polypropylene, polyvinyl acetal, polyvinyl butyral, polyvinylchloride and the like.

Other features can be incorporated into the support system for the lamp as shown in FIG. 1. For example, a tubular sleeve 27 may be inserted over the exterior surface of the trunk and arms of the lamp to provide protection means to the tubular connectors. The tubular sleeve protective covering provides a mechanism for reducing contamination due to infectious material lodging in the intricate crevices of the tubular connectors and reduces cleaning problems associated with the trunk and the arms pendent from the trunk which carry equipment associated with the multifunctional lamp. Examples of protective coverings include polymeric materials and heat shrinkable tubing. In addition, because of the tubular structure of the support system comprising the trunk and arms, means for stiffening communicating with said trunk can be provided. Often the means for stiffening are inserted interior to the trunk or any of the arms which then restricts movement about the X and Z-axis but permits rotation about the Y-axis or longitudinal axis. The means for stiffening may be of indeterminate length depending upon the need for support at a fixed distance from the base. Generally the means for stiffening anywhere up to about three quarters of the length of the trunk or less. Examples of stiffening means include steel and other metal or polymeric rods and/or tubes which are rigid relative to the trunk and arms and securely fastened to the base. Examples of protective sleeve materials include polyethylene, polypropylene, polyvinylchloride, polyvinylidene chloride film and the like.

Electrical communication with the illumination source and microphone can be achieved by inserting wires through the tubular portion of the trunk and pendent arms. One mechanism for providing electrical communication through the trunk and arm portions is through a Tee-member (not shown) near the base of the lamp which readily permits the insertion of electrical wires, etc. into the tubular portion of the trunk and arms. Once electrical communication is established, illumination and other equipment requiring electrical power may be utilized. Another embodiment contemplates the addition of another arm for purposes enhancing lamp functionality. A magnet or clamp may be such a device pendent from the unused arm.

What is claimed is:

1. In a lamp comprising a base, a tubular trunk, and an illumination source wherein an end of said tubular trunk is in supportable communication with said base and another end portion of said tubular trunk is in communication with said illumination source, the improvement which comprises a multifunctional lamp particularly suited for medical use which comprises:

said tubular trunk supported by the base, said tubular trunk formed from a plurality of interconnecting tubular connectors joined end to end, each tubular connector having a ball portion at one end and a socket portion at the other end, said ball portion adapted for frictional embracement by a socket portion associated with an adjoining tubular connector;

a plurality of tubular Tee-members having distal ball or socket portions engaged by a corresponding socket or ball portion from tubular connectors associated with the tubular trunk of said lamp, said tubular Tee-members adapted for rotation and flexible movement about the longitudinal axis of the tubular trunk;

a first tubular arm supported and pendent from said tubular trunk comprising a plurality of tubular connectors having ball and socket portions with the ball or socket member of said first tubular arm engaging a corresponding socket or ball portion associated with said Tee-members and terminating in means for engaging a safety shield; and, a second tubular arm supported and pendent from said tubular trunk comprising a plurality of tubular connectors having ball and socket portions with an end portion adapted for engaging socket or ball portions associated with said tubular Tee-members and an end portion terminating in means for magnification.

2. The lamp of claim 1 wherein a third arm is pendent from said tubular trunk of said lamp and said third arm carries a microphone.

3. The lamp of claim 1 wherein the second tubular arm pendent from said tubular trunk carries a magnifying glass.

4. The lamp of claim 1 wherein said tubular trunk has a polymeric protective sleeve over its exterior surface for the protection of said tubular trunk.

5. The lamp of claim 1 wherein means for stiffening said tubular trunk are associated with said tubular trunk and communicates with a portion thereof.

6. The lamp of claim 5 wherein the means for stiffening said trunk comprises a rigid metal rod inserted within the interior of said trunk and rigidly secured to said base thereby stiffening the interior of the trunk.

7. The lamp of claim 5 wherein the base is a magnet having a polymeric substrate applied to its base surface.

8. In a flexible support system comprising a tubular trunk supported by a base, the improvement which comprises:

said tubular trunk formed from a plurality of interconnecting tubular connectors joined end to end, each tubular connector having a ball portion at one end and a socket portion at the other end, said ball portion adapted for frictional embracement by a socket portion associated with an adjoining tubular connector; and, means for stiffening said tubular trunk comprising a rod communicating with a portion of said tubular trunk, said rod being disposed interior to tubular trunk, being rigid relative to said tubular trunk and secured at an end to said base.

9. The support system of claim 8 wherein a polymeric sleeve is placed over the exterior surface of the trunk.

10. The support system of claim 8 wherein an end of said trunk terminates in a protective shield.

* * * * *